United States Patent [19]

Trowbridge

[11] 4,434,156
[45] Feb. 28, 1984

[54] MONOCLONAL ANTIBODIES SPECIFIC FOR THE HUMAN TRANSFERRIN RECEPTOR GLYCOPROTEIN

[75] Inventor: Ian S. Trowbridge, San Diego, Calif.

[73] Assignee: The Salk Institute for Biological Studies, San Diego, Calif.

[21] Appl. No.: 315,194

[22] Filed: Oct. 26, 1981

[51] Int. Cl.³ .................... C12N 5/02; A61K 39/395
[52] U.S. Cl. .............................. 424/85; 260/112 R; 435/68; 435/240; 435/172; 436/547; 436/548
[58] Field of Search ................... 424/1, 1.5, 1.1, 85; 436/548, 547; 435/240, 68

[56] References Cited

U.S. PATENT DOCUMENTS

| | | | |
|---|---|---|---|
| 4,332,785 | 6/1982 | Allen | 435/7 |
| 4,361,550 | 11/1982 | Kung et al. | 260/112 R |
| 4,364,933 | 12/1982 | Kung et al. | 260/112 R |
| 4,364,934 | 12/1982 | Kung et al. | 260/112 R |
| 4,364,935 | 12/1982 | Kung et al. | 260/112 R |
| 4,364,936 | 12/1982 | Kung et al. | 260/112 R |
| 4,364,937 | 12/1982 | Kung et al. | 260/112 R |

OTHER PUBLICATIONS

Omary, M. B. et al., Nature, vol. 286, pp. 888-891, (8-1980), (B3/25).
Reinherz, E. J. et al., Proc. Natl. Acad. Sci., vol. 77(3), pp. 1588-1592, (3-1980), OKT9.
Haynes, B. F. et al., J. Immunology, vol. 127(1), pp. 347-351, (07-1981).
Sutherland, R. et al., Proc. Natl. Acad. Sci., vol. 78(7), pp. 4515-4519, (07-1981).
Cotner, T. et al., Journal of Experimental Medicine, vol. 157, pp. 461-472, (2-1983), See p. 469.
Trowbridge, I. S. et al., Nature, vol. 294 (1981), pp. 171-173.

Primary Examiner—Benjamin R. Padgett
Assistant Examiner—M. Moskowitz
Attorney, Agent, or Firm—Fitch, Even, Tabin & Flannery

[57] ABSTRACT

Monoclonal antibodies are produced specific for the cell surface transferrin receptor of human cells. Animals are inoculated with purified human transferrin receptor glycoprotein, human hematopoietic cells or fragments thereof, and spleen cells obtained from the animals are fused with myeloma cells to produce hybridomas. The hybridomas are cultured as clones, and antibodies obtained from the individual clones are tested for their specificty for human transferrin receptor. Clones which produce antibodies specific for the receptor and that interfere with or block transferrin binding are selected for further culturing to produce the antibody, and the antibody is obtained from the culture growth medium or from ascitic fluid of an animal bearing a tumor of the hybridoma. Monoclonal antibodies which block transferrin binding are useful in regulating cell growth and for other therapeutic uses.

16 Claims, No Drawings

MONOCLONAL ANTIBODIES SPECIFIC FOR THE HUMAN TRANSFERRIN RECEPTOR GLYCOPROTEIN

The present invention is related to monoclonal antibodies and a novel application of such antibodies as growth regulatory drugs.

BACKGROUND OF THE INVENTION

Antibodies have long been used in medical diagnosis, e.g., determining blood types, and in biological experimentation. The usefulness of antibodies, however, has been somewhat limited, as their complexity and diversity have made it very difficult to obtain homogeneous antibodies. Antibodies are complex protein or protein-based molecules which are produced by the immune systems of animals to protect the animal against foreign substances. Antibodies for medical use are generally obtained by injecting an animal with a foreign substance which will stimulate the animal's immune system, and, most commonly, isolating an antibody fraction from the peripheral blood serum or from the ascitic fluid. The antibody fraction contains antibodies specific to the injected foreign substance as well as various other antibodies produced by the animal, and by known techniques, it may be possible to substantially isolate an antibody specific to the particular foreign substance. However, even when an antibody for a particular foreign substance is isolated, such antibody is actually a mixture of several antibodies which recognize various antigenic determinants of the foreign substance or related substances. While some individual antibody molecules may be highly specific, recognizing only a certain foreign substance or portion thereof, other antibody molecules may be less selective, recognizing not only the subject foreign substance but other substances as well. Since it is generally practically impossible to separate all related antibodies, even the most carefully purified antibody fractions may react with more than one substance.

In recent years, techniques of producing monoclonal antibodies have been developed which make it possible to obtain homogenous, highly specific antibodies. Kohler G. and Milstein, C.: (1975) Nature 256 495-497. Generally, such antibodies are produced by immunizing an animal with a protein fraction or other foreign substance, obtaining antibody-producing cells from the animal, and fusing the antibody producing cells with strains of myeloma cells, e.g., tumor cells, to produce hybridomas which are isolated and cultured as monoclones. The monoclonal hybridomas may either be cultured in vitro or may be grown as tumors in a host animal. Since each antibody-producing cell produces a single unique antibody, the monoclonal cultures of hybridomas each produce a homogenous antibody which may be obtained either from the culture medium of hybridoma cultures grown in vitro or from the cells, ascitic fluid, or serum of a tumor bearing host animal.

Not all of the hybridoma clones which result from fusing neoplastic cells with antibody producing cells are specific for the desired foreign substance or antigen (a substance with which the antibody reacts) since many of the hybridomas will make antibodies which the animal has produced to react with other foreign substances. Even antibodies against the subject antigen will differ from clone to clone since antibodies produced by different cells may react with different antigenic determinants of the same molecule. From each clone, therefore, it is necessary to obtain the resulting antibody or the antibody-containing medium, serum or ascitic fluid and test its reactivity with the subject antigen and to test its specificity by determining with what other substances, if any, it recognizes. While the necessity of characterizing the antibody of each clone adds to the complexity of producing monoclonal antibodies, the wide variety of homogeneous antibodies which may be obtained gives investigators a number of very precise tools to map the structure and development of somatic cells.

The availability of homogeneous, highly specific monoclonal antibodies increases the value of antibodies as diagnostic, experimental and therapeutic tools. Use of monoclonal antibodies for tumor and virus detection have been described in U.S. Pat. Nos. 4,172,124 and 4,196,265.

Monoclonal antibodies are particularly suitable for studying the pathways and processes by which cells differentiate into different types of somatic cells to produce the various tissues of the body. Cell differentiation is a complex subject, and understanding of the processes are only beginning. Proteins which are specific to particular cell types and which may be detected by different monoclonal antibodies, serve as precise markers for the study of cell development and differentiation. Monoclonal antibodies which are specific for given proteins not only may be used to ascertain the presence of known proteins in a cell, but may be used to detect substances heretofore undiscovered. Theoretically it may be possible to eventually obtain monoclonal antibodies for every macromolecule in the body to permit the complete mapping of the various proteins, etc.

An important topic in the field of cell differentiation is the study of cells which, in their mature form, are non-proliferating being derived from actively proliferating stem cells. Many examples of such cells may be found in the peripheral blood. Red blood cells and leukocytes arise from stem cells in the bone marrow and both are normally non-proliferating as mature cells in the blood stream. Misdevelopment of somatic cells may lead to cancers, including blood cell related cancers such as myelomas and leukemias, and monoclonal antibodies are useful in determining the proteins present in such cell to more fully trace their development and derivation.

It is a primary object of the present invention to create and culture hybridomas which produce monoclonal antibodies that react with the human transferrin receptor blocking transferrin binding to the cells and interfering with the ability of the cells to proliferate. The long term objective is to use these antibodies to regulate cell growth in proliferative diseases in vivo particularly in the treatment of cancer.

SUMMARY OF THE INVENTION

Monoclonal antibodies are produced which are specific for the human transferrin receptor. Mice are inoculated with human transferrin receptor glycoprotein, and spleen cells or lymph node cells are obtained from the inoculated mice and fused with mice tumors. Monocultures of the fused cells are produced, and the antibodies obtained from the monoclones are tested for their ability to react with the human transferrin receptor and block transferrin binding in order to select the monocultures which produce antibodies with the desired characteristics. The monoclonal antibodies are useful for killing or regulating the growth of human cells, in particular tumor cells.

DETAILED DESCRIPTION OF THE PREFERRED EMBODIMENTS

Monoclonal antibodies are produced which are specific for the human transferrin receptor, which is found on the surface of dividing cells particularly proliferating tumor cells. The transferrin receptor glycoprotein has been characterized as having a monomer molecular weight of about 95,000, as determined by its migration on SDS polyacrylamide gel, and existing in its native state as a disulphide bonded dimer. Omary et al., (1980) Nature 286, 888–891; Judd et al., (1980) J. Exp. Med. 152 1430–1435; Trowbridge and Omary (1981) Proc. Nat. Acad. Sci. U.S.A. 78 3039–3043; Sutherland et al. (1981) Proc. Nat. Acad. Sci. U.S.A. 78 4515–4519.

Purified human transferrin receptor glycoprotein is introduced into animals, to induce the production of antibodies to the glycoprotein, which is found on the surface of the hematopoietic cells. Any immunogen containing human transferrin receptor glycoprotein or crossreactive material including intact human cells may also be used instead of purified receptor although the latter is preferred. The animal chosen for inoculation is not critical, but it is preferred to use strains of murines, i.e. rats, mice, etc. which are well characterized. Furthermore, various murine-derived neoplastic cells are also available as well-characterized cultures. Hence, mice are chosen for production of the antibodies hereindescribed, although it is to be understood that the invention is not limited to murine developed antibodies.

BALB/c mice are inoculated subcutaneously with 50 g purified human transferrin receptor isolated from CCRF-CEM cells as described by Trowbridge and Omary (1981) supra mixed with complete Freunds adjuvant, and after 6 weeks, the mice are inoculated with a booster of at least 50 $\mu$g purified receptor given intravenously in saline. Four days after the second inoculation, the mice are sacrificed and their spleens are taken. A spleen cell suspension is prepared, and the resulting cell suspension is washed by two centrifugations (800×g) in protein-free Dulbecco's modified Eagles medium.

Since the antibody-producing cells obtained from the spleen do not independently reproduce, and thus cannot be cultured, they are fused with cells which may be independently cultured either in vivo or in vitro so that the genetic and metabolic processes of the fused hybridomas have characteristics of each of the parent cells, and it is intended that certain of the cells obtained will have the capability to independently reproduce and to produce the antibody of the antibody-producing parent cell. Some tumor cells, particularly myeloma cells, may be advantageously fused with antibody-producing cultures of hybridomas. Although it is not necessary, it is preferred that the tumor cells and antibody-producing cells be derived from the same species to enhance the likelihood that the genetic and biochemical properties of the parent cells will be compatible and thus produce viable hybridomas. A number of myeloma cultures have been characterized, and herein, mouse-derived nonantibody-producing myeloma cell line S194 5.XXO.BU.1 (Trowbridge, J. Exp. Med., 148, 313–323 (1978)), samples of which are on deposit at the Salk Institute Cell Distribution Center, are used to produce the hybridomas. It is to be understood that other tumor lines, which include but are not limited to P3, Y3, SP2/0, MPC-11 and their derivatives, may also be used.

It is advantageous to select a myeloma line which does not produce antibody so that the resulting hybrid will only produce antibody chains of the parent spleen or lymph node cell. This is particularly important when the antibody is used for therapeutic purposes, e.g., to regulate cell growth, where it is undesirable to introduce extraneous antibodies which could produce side reactions.

The myeloma cells are maintained in Dulbecco's modified Eagles's medium supplemented with 10% horse serum. $10^7$ myeloma cells and $10^8$ cells obtained from the mice immunized with human transferrin receptor are resuspended for fusion in a 45% solution (v/v) of polyethylene glycol 1500 according to the methods of Trowbridge (1978) supra. Cell hybrids are selected in hypoxanthine aminopterin thymidine (HAT) medium, all growth in HAT medium being indicative of successful hybridization of mouse spleen and mouse myeloma cells, and their production of antibodies against CCRF-CEM cells, from which the purified transferrin receptor used to inoculate the mice was isolated, is tested by the antibody binding assay described by Williams et al., Cell 12, 663 (1977). Hybrid cells are cloned by the method of limiting dilution in Falcon microtiter plates.

Clones of hybridomas may be grown in vitro according to known tissue culture techniques such as is described by Cotten et al. Eur. J. Immunol. 3, 136 (1973). Alternatively, hybridomas may be grown in vivo as tumors in a histocompatible animal or in athymic nude mice. The antibodies may be recovered from the in vitro culture medium or from the serum or ascitic fluid of the animal by means known in the art, e.g., Gerhard et al., Proc. Natl. Acad. Sci., 75, pp. 1510–1514 (1978). In some cases it may be advantageous to obtain the antibodies directly from the cells of the culture or tumor.

The specificity of the antibody from each clone for CCRF-CEM is examined by the methods of Williams supra., and clones which produce antibody specific for CCRF-CEM cells are selected. Antibodies binding to CCRF-CEM cells are then tested for their reactivity with the human transferrin receptor by determining whether they will immunoprecipitate the receptor from Nonidet P-40 lysates of CCRF-CEM cells previously surface labeled with $^{125}$I by the lactoperoxidase technique. These methods are described by Trowbridge and Omary, (1981) supra. and are standard precedures. Antibodies are then tested to determine whether they block transferrin binding by the following method. CCRF-CEM cells ($5 \times 10^5$) are incubated with 50 $\mu$l tissue culture supernates containing monoclonal antibody for 45 minutes at 4° C. Cells are then centrifuged three times to remove unbound antibody. Washed cells are then incubated 45 minutes at 4° C. with $^{125}$I-labeled human transferrin (about $1 \times 10^6$ cpm of labeled transferrin with a specific activity of about 1 $\mu$Ci per $\mu$g) in 100 $\mu$l 0.15 M NaCl 0.01 M phosphate buffer (pH 7.2). Cells are then washed three times, and the radioactivity bound to cells incubated with the antibody is compared to control cells that were incubated with tissue culture medium without antibody. Monoclonal antibodies which block transferrin binding, based on a reduced amount of $^{125}$I-labeled transferrin bound to cells in this assay, are selected.

When a useful hybridoma clone is produced it is generally advantageous to reclone the cell line to avoid overgrowth of cultures with variant cells no longer producing antibody. Since the hybridoma contains some, but not all, of the genetic material of each parent cell, the full characteristics of the hybridoma are not known. Often a hybridoma clone, due to original genetic deficiency or subsequent chromosome loss, after several passages may lose its ability to reproduce and or to produce the particular antibody. Accordingly, it is important, soon after the initial hybridization, that a hybridoma clone of interest is recloned to insure the availability of functioning strains of the antibody-producing hybridoma. A cell line culture identified as 42/6 and its derivatives produce a monoclonal antibody specific for transferrin receptor glycoprotein that blocks transferrin binding. The 42/6 cell line is on deposit at the American Tissue Culture Collection of 12301 Parklawn Drive, Rockville, Md. 20852 and has been given the accession number HB-8094.

Trace antibody binding assays conducted according to the methods of Morris et al., Eur. J. Immunol. 5, 274–281 (1974) demonstrate the general reactivity of the 42/6 monoclonal antibody with human CCRF-CEM leukemic cells. Immunoprecipitation studies and the blocking assay, described earlier, demonstrate that 42/6 monoclonal antibody reacts with the human transferrin receptor and blocks binding of transferrin.

The following two examples demonstrate that the 42/6 monoclonal antibody blocks transferrin binding to its receptor on CCRF-CEM cells and further demonstrates that this antibody can thus regulate the growth of these tumor cells in vitro.

EXAMPLE I

CCRF-CEM cells are washed in 0.15 M NaCl 0.01 M phosphate buffered (PBS) pH 7.2. Cells are resuspended in PBS, each sample having $5 \times 10^5$ cells in 50 $\mu$l of solution, and 50 $\mu$l of Dulbecco's modified Eagles medium supplemented with 10% horse serum and containing different dilutions of 42/6 monoclonal antibody is added. As controls, cells are resuspended in PBS alone or PBS containing 15 $\mu$g of unlabeled human transferrin. All of the samples are incubated at 4° C. for 45 minutes. Cells then pelleted by centrifugation and washed three times with PBS containing 15 mM NaN and 0.1% bovine serium albumin. The washed cells are incubated for 45 minutes at 4° C. with 100 $\mu$l of a 1:200 dilution in PBS of $^{125}$I-labeled human transferrin (400 $\mu$g/ml; 1 Ci/$\mu$g), then washed three times more and the bond radioactivity counted in a gamma counter. The results are shown in Table I.

TABLE I

| Reciprocal Dilution of 42/6 antibody (initial concentration 8 g/ml) | concentration of unlabeled human transferrin | $^{125}$I-labeled transferrin bound |
|---|---|---|
| 1 | | 568 |
| 2 | | 593 |
| 3 | | 644 |
| 4 | | 676 |
| 5 | | 826 |
| 6 | | 967 |
| 7 | | 1383 |
| 8 | | 1661 |
| 9 | | 1802 |
| 10 | | 2126 |
| 11 | | 2087 |
| | None | 2018 |
| | 15 $\mu$g/ml | 1008 |

The control series in which the cells were incubated with unlabeled transferrin shows that prior occupation of transferrin binding sites reduces the amount of transferrin which is later bound. The test series in which the cells were incubated with various amounts 42/6 monoclonal antibody shows that the antibody, like transferrin, prevents access to transferrin binding sites thereby reducing the amount of transferrin which may later be bound.

EXAMPLE 2

CCRF-CEM, a human T leukemic cell line was set up at $7.2 \times 10^4$ cells per ml in RPMI 1640 tissue culture medium supplemented with 10% horse serum. All cultures were made 50% in Dulbecco's modified Eagles medium containing various amounts of 42/6 monoclonal antibody. Cell growth was monitored by counting the cells in duplicate dishes in a Coulter counter. The results are summarized in Table II below

TABLE II

| Concentration of 42/6 antibody ($\mu$g/ml) | number of cells/ml $\times 10^4$ Day 0 | number of cells/ml $\times 10^4$ Day 5 | number of cells/ml $\times 10^4$ Day 7 |
|---|---|---|---|
| 0 | 7.2 | 44 | 100 |
| 2 | 7.2 | 17.7 | 25 |
| 4 | 7.2 | 16.5 | 16.2 |
| 8 | 7.2 | 12 | 12.3 |

The above results demonstrate that 42/6 monoclonal antibody profoundly inhibits the growth of cells having transferrin receptor glycoprotein. In view of the results of Example 1, it appears that the inhibition of cell growth by the monoclonal antibody is achieved by blocking the transferrin receptor sites.

Analysis of the cell cycle position of the antibody treated cells by mithramycin staining by the method of Crossman H. and Tobey. R. (1974) Science 184, 1297–1298 showed that the cells treated with the highest concentration of antibody were accumulated in the S phase of the cell cycle suggesting that the antibody was interfering with the ability of the cells to synthesize DNA. Lesser amounts of antibody resulted in fewer cells in the S phase and a less complete inhibition of growth.

Since the human transferrin receptor is expressed in certain cancer tumors, 42/6 antibody is applicable for various cancer diagnostic applications. Since transferrin receptors are generally not expressed on the peripheral blood cells, the presence of transferrin receptor glycoprotein-containing cells in the blood stream, as determined by radioimmunoassay, may indicate the presence of cancer cells. Due to the highly specific nature of monoclonal antibodies, individual cancer cells may be complexed with radioactivity labeled antibody and detected, as by autoradiography, before the cancer is detectable by conventional methods. Immunofluorescence techniques using the anti-transferrin receptor antibody are useful in determining the source and type of cancer cell in tumor biopsy. $^{125}$I-labeled monoclonal 42/6 transferrin receptor of glycoprotein-specific antibody may be used to detect metastases by X-ray imaging as described by Levine, et al., Science, 206, 846 (1979).

Therapeutic applications of anti-transferrin receptor monoclonal antibodies include conventional immunotherapy, where a class of antibody is used to destroy the tumor cells by complement-mediated lysis or other effector mechanisms, and immunotherapy where a cytotoxic agent such as methotrexate or ricin toxin is carried by the monoclonal antibody to destroy tumor cells (e.g., Trowbridge and Domingo (1981) Nature in press).

In particular, monoclonal antibodies which block transferrin binding to the transferrin receptor may be administered to mammals in a therapeutically effective dose for interfering with the growth of human tumor cells by starving them of iron or some other regulatory mechanism. The 42/6 antibody is also useful for arresting tumor cells in S phase of the cell cycle and thus rendering them sensitive to other chemotherapeutic agents. Other potential uses of the 46/2 monoclonal antibody that can be envisaged are the treatment of iron-storage diseases such as hereditary hemochromatosis and in the disease states such as graft-versus-host reaction.

Modifications obvious to one with ordinary skill in the art may be made without departing from the scope of the present invention. For example, antibody production may be induced in the host animal by inoculating the animal with other human cell lines containing the transferrin receptor glycoprotein or with cell membrane fragments or cell membrane derived material rather than with complete hematopoietic cells or isolated human transferrin receptor glycoprotein.

While the invention has been described in terms of human transferrin receptor, the methods are equally applicable to producing antibodies useful in detecting related non-human transferrin receptor or siderophores and inhibiting cell growth.

Various features of the invention are set forth in the following claims.

What is claimed is:

1. A method of producing monoclonal antibodies specific for the transferrin binding site of human transferrin receptor glycoprotein and which block binding of transferrin to the glycoprotein, the method comprising
   inoculating a rodent animal with material containing said transferrin receptor glycoprotein,
   obtaining antibody-producing cells from said animal,
   fusing said antibody-producing cells and neoplastic cells to produce hybridomas,
   selecting hybridomas that produce an antibody which reacts with said transferrin binding site and blocks subsequent binding of transferrin to the glycoprotein,
   producing clones of said selected hybridomas, and
   collecting the antibodies produced thereby.

2. A method according to claim 1 wherein said antibody-producing cells are BALB/C mouse spleen cells.

3. A method according to claim 1 wherein said transferrin receptor glycoprotein is obtained from the group of human hematopoietic cells and human hematopoietic cell membrane material.

4. A method according to claim 3 wherein said human hematopoietic cell line is CCRF-CEM.

5. A method according to claim 1 wherein said neoplastic tissue cells are of the non producer myeloma cell line, S194/5.XXO.BU.1.

6. A method according to claim 1 wherein said clones are grown in host animals, and said antibody is obtained from the group consisting of the host animal's blood serum and the host animal's ascitic fluid.

7. A cell line produced by the fusion of an antibody-producing rodent animal cell and a neoplastic cell, which produces a rodent antibody specific for the transferrin binding site of the human transferrin receptor glycoprotein and which blocks binding of transferrin to the receptor glycoprotein.

8. A cell line according to claim 7 wherein said antibody-producing cell is derived from the murine genus.

9. A cell line according to claim 7 wherein said antibody-producing cells are selected from the group of murine spleen cells and murine lymph node cells.

10. A cell line according to claim 7 wherein said antibody-producing cells are BALB/c mouse spleen cells.

11. A cell line according to claim 7 wherein said neoplastic cell is non antibody producing.

12. A cell line according to claim 7 selected from the group consisting of HB-8094 hybridoma and antibody-producing reclones thereof.

13. Rodent monoclonal antibodies specific for the transferrin binding site of human transferrin receptor glycoprotein and which block binding of transferrin to the receptor glycoprotein.

14. Monoclonal antibodies according to claim 13 obtained from cultures selected from the group consisting of HB-8094 hybridoma and antibody-producing reclones thereof.

15. A method of regulating cell growth in a mammal comprising administering a therapeutically effective does of a rodent monoclonal antibody that is specific to the transferrin binding site of human transferrin receptor glycoprotein and blocks transferrin binding to the receptor glycoprotein.

16. A method according to claim 15 wherein said antibody is obtained from HB-8094 hybridoma or antibody-producing reclones thereof.

* * * * *

UNITED STATES PATENT AND TRADEMARK OFFICE
CERTIFICATE OF CORRECTION

PATENT NO. : 4,434,156  
DATED : February 28, 1984  
INVENTOR(S) : Ian S. Trowbridge It is certified that error appears in the above-identified patent and that said Letters Patent is hereby corrected as shown below:

Column 1, line 59, "tumor bearing" should read --tumor-bearing--.

Column 1, line 61, "antibody producing" should read --antibody-producing--.

Column 2, line 26, after "antibodies" the comma (,) should be deleted.

Column 2, line 31, after "Theoretically" a comma (,) should be inserted.

Column 2, line 43, after "cancers" (second instance) a comma (,) should be inserted.

Column 2, line 45, "in" should read --for--.

Column 2, lines 52-53, "long term" should read --long-term--.

Column 2, line 54, after "in vivo" a comma (,) should be inserted.

Column 2, line 62, "tumors" should read --tumor cells--.

Column 3, line 8, after "cells" a comma (,) should be inserted.

UNITED STATES PATENT AND TRADEMARK OFFICE
CERTIFICATE OF CORRECTION

PATENT NO. : 4,434,156

DATED : February 28, 1984

INVENTOR(S) : Ian S. Trowbridge

It is certified that error appears in the above-identified patent and that said Letters Patent is hereby corrected as shown below:

Column 3, line 19, after "animals" the comma (,) should be deleted.

Column 3, line 20, after "glycoprotein" the comma (,) should be deleted.

Column 3, line 23, after "material" a comma (,) should be inserted.

Column 3, line 24, after "receptor" a comma (,) should be inserted.

Column 3, line 32, "murine developed" should read --murine-developed--.

Column 3, lines 33-34, "50 g" should read --50μg--.

Column 3, line 36, "Freunds" should read --Freund's--.

Column 3, line 43, "Eagles" should read --Eagle's--.

Column 4, line 59, after "cells" insert --which were--.

Column 4, line 65, after "produced" a comma (,) should be inserted.

Column 5, line 5, "and or" should read --and/or--.

Column 5, line 35, "Eagles" should read --Eagle's--.

UNITED STATES PATENT AND TRADEMARK OFFICE
CERTIFICATE OF CORRECTION

PATENT NO. : 4,434,156

DATED : February 28, 1984

INVENTOR(S) : Ian S. Trowbridge

It is certified that error appears in the above-identified patent and that said Letters Patent is hereby corrected as shown below:

Column 5, line 43, correct the spelling of --serum--.

Column 5, line 47, "bond" should read --bound--.

Column 6, line 3, after "sites" a comma (,) should be inserted.

Column 6, line 11, "Eagles" should read --Eagle's--.

Column 6, line 37, after "cycle" a comma (,) should be inserted.

Column 6, line 66, after "agent" a comma (,) should be inserted.

Column 6, line 68, "in press" should read --(London) 294, 171-173 (1981)--.

Column 7, line 7, after "in" insert --the--.

Column 7, line 11, after "diseases" a comma (,) should be inserted.

Column 7, line 19, "membrane derived" should read --membrane-derived--.

UNITED STATES PATENT AND TRADEMARK OFFICE
CERTIFICATE OF CORRECTION

PATENT NO. : 4,434,156
DATED : February 28, 1984
INVENTOR(S) : Ian S. Trowbridge It is certified that error appears in the above-identified patent and that said Letters Patent is hereby corrected as shown below:

Column 7, line 46, "BALB/C" should read --BALB/c--.

Column 8, line 6, "non producer" should read --non-producer--.

Column 8, line 21, after "group" --consisting-- should be inserted.

Column 8, line 41, change "does" to --dose--.

Signed and Sealed this

Thirteenth Day of November 1984

[SEAL]

Attest:

*Attesting Officer*

GERALD J. MOSSINGHOFF

*Commissioner of Patents and Trademarks*